(12) United States Patent
Dekeyser et al.

(10) Patent No.: US 7,592,374 B2
(45) Date of Patent: Sep. 22, 2009

(54) INSECTICIDAL NITROMETHYLENE COMPOUNDS

(75) Inventors: Mark A. Dekeyser, Waterloo (CA); Sheldon B. Park, Guelph (CA); Paul T. McDonald, Middlebury, CT (US)

(73) Assignee: Crompton Corporation, Middlebury, CT (US)

( * ) Notice: Subject to any disclaimer, the term of this patent is extended or adjusted under 35 U.S.C. 154(b) by 887 days.

(21) Appl. No.: 11/072,575

(22) Filed: Mar. 3, 2005

(65) Prior Publication Data

US 2006/0199850 A1     Sep. 7, 2006

(51) Int. Cl.
*A61K 37/52* (2006.01)
*A01N 33/02* (2006.01)
*C07C 245/00* (2006.01)

(52) U.S. Cl. .................. 514/637; 514/638; 514/639; 534/558; 534/559

(58) Field of Classification Search .......... 514/637, 514/638, 639; 534/558, 559
See application file for complete search history.

(56) References Cited

U.S. PATENT DOCUMENTS

| | | | |
|---|---|---|---|
| 2,547,724 A | 4/1951 | Sundholm | 167/33 |
| 2,548,480 A | 4/1951 | Kittleson et al. | |
| 3,641,098 A | 2/1972 | Buchel et al. | 260/465 |
| 3,786,131 A | 1/1974 | Buchel et al. | 424/304 |
| 4,426,393 A | 1/1984 | Troiani et al. | 424/327 |
| 4,725,302 A | 2/1988 | Ehrenfreund | 71/88 |
| 5,367,093 A | 11/1994 | Dekeyser et al. | 560/27 |
| 5,536,746 A | 7/1996 | Dekeyser et al. | 514/468 |
| 5,567,723 A | 10/1996 | Dekeyser et al. | 514/357 |
| 6,093,843 A | 7/2000 | Chee et al. | 560/27 |
| 6,297,275 B1 | 10/2001 | Dekeyser et al. | 514/486 |
| 6,706,895 B1 | 3/2004 | Park et al. | 549/75 |

FOREIGN PATENT DOCUMENTS

| | | |
|---|---|---|
| CA | 1177851 | 11/1984 |
| CN | 1035660 | 9/1989 |
| EP | 0067471 | 5/1982 |
| GB | 1160648 | 5/1967 |

OTHER PUBLICATIONS

*Chemical Abstracts*, vol. 108, No. 19, p. 249, Item 163280 (1988). Abstract for SU1192309A published Mar. 30, 1988.
*Chemical Abstracts*, vol. 113, No. 21, p. 680, Item 190943 (1990).
*Chemical Abstracts*, vol. 105, No. 17, p. 659, Item 152686 (1986).
*Chemical Abstracts*, vol. 71, No. 15, p. 282, Item 70292 (1969).
*Chemical Abstracts*, vol. 72, No. 15, p. 362, Item 78682 (1970).
*Chemical Abstracts*, vol. 76, No. 7, p. 77, Item 31221 (1972).
*Chemical Abstracts*, vol. 93, No. 5, p. 208, Item 38256 (1980).
*Chemical Abstracts*, vol. 102, No. 19, p. 590, Item 166449 (1985).
*Chemical Abstracts*, vol. 106, No. 15, p. 217, Item 115102 (1987).

*Primary Examiner*—Sabiha Qazi
(74) *Attorney, Agent, or Firm*—Jaimes Sher

(57) ABSTRACT

A composition of matter is disclosed that comprises a compound of the formula:

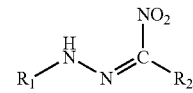

wherein $R_1$ is selected from the group consisting of unsubstituted and substituted biphenyl moieties, unsubstituted and substituted fluorenyl moieties, unsubstituted and substituted carbazolyl moieties, and unsubstituted and substituted pyridyl moieties; and $R_2$ is hydrogen or alkyl.

The compositions are useful as insecticides, acaricides, and fungicides.

17 Claims, No Drawings

INSECTICIDAL NITROMETHYLENE COMPOUNDS

BACKGROUND OF THE INVENTION

1. Field of the Invention

The present invention relates to novel nitromethylene compounds that exhibit activity as insecticides, acaricides, and fungicides. The invention also relates to insecticidal, acaricidal, and fungicidal compositions comprising such nitromethylene compounds.

2. Description of Related Art

Destruction by insects, acarids and fungi presents a serious problem to agriculture. A wide variety of field crops are in need of protection from fungi, acarids, and insects including such valuable crops as soybeans, corn, peanuts, cotton, alfalfa, rice and tobacco. In addition, vegetables, such as tomatoes, potatoes, sugar beets, carrots, peas, and the like, as well as fruits, nuts, ornamentals, and seed bed crops, such as apples, peaches, almonds, citrus fruit and grapes may also require protection from the ravages of such pests.

Consequently, the development of new, more effective pesticides including insecticides, acaricides, and fungicides represents an ongoing scientific activity. More particularly, the development of pesticides which are effective as both ovicides and larvicides are of interest.

Chemical Abstracts 108(19):163280d refers to alkyl phenylhydrazinecarboxylates said to be useful as acaricides. U.S. Pat. No. 4,725,302 refers to substituted phenylhydrazines and phenyloxadiazolinones said to be useful as pesticides. European Patent 0 067 471 refers to 7-substituted 2,3-dihydrobenzofurans said to be useful as pesticides or chemical intermediates. DerWent abstract 88-312695/44 refers to arylhydrazides of trifluoroacetic acid said to have fungicidal, bacteriocidal, acaricidal, and antiseptic activity. Chemical Abstracts 105(17):152686c refers to various phenylhydrazines said to have activity against insects and mites.

Certain nitromethylene compounds which show insecticidal and fungicidal properties have been described in the following references: CA 71:70292, CA 72:78682, CA 76:31221, CA 93:38256, CA 102:166449, CA 106:115102, and CA 113:190943.

U.S. Pat. Nos. 3,641,098 and 3,786,131 disclose α-(halo, cyano, nitro, and azido)-α-(alkanoyl, carboalkoxy [i.e., alkoxy carbonyl], amino and mono- and di-alkyl amino)-carbonyl-(unsubstituted and mono to penta alkyl and/or electronegative substituent [e.g., halo, nitro, cyano, trifluoromethyl, trifluoromethyl-, -mercapto, -sulfonyl and -sulfoxyl, alkoxy, alkyl sulfonyl and/or dimethylaminosulfonyl sulfonyl]-substituted) phenyl hydrazones and their corresponding alkali metal, alkaline earth metal and amine salts, which are said to possess pesticidal, especially acaricidal and insecticidal, properties and which can be produced by conventional methods.

U.S. Pat. No. 4,426,393 discloses arylhydrazo-aldoximes which, as such, as tautomers, and in the form of organic or inorganic salts thereof, are said to be active in preventing and treating infections of useful plants by fungi, and in immunizing plants against such infections.

U.S. Pat. Nos. 5,367,093 and 5,536,746 disclose compounds having the structural formulae

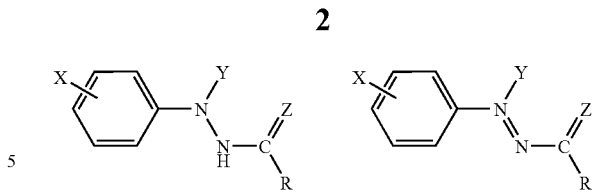

wherein:

X is a) phenyl; lower phenylalkoxy; phenoxy; or benzyl; or b) one substituent from group a) and one or more substituents selected from $C_1$-$C_4$ alkoxy; halogen; lower alkyl; and lower alkylthio; or c) along with the phenyl to which it is attached, forms a multiple fused ring heterocycle such as dibenzofuranyl;

Y is H, $C_1$-$C_4$ alkanoyl, $C_1$-$C_4$ haloalkanoyl, dialkoxyphosphoryl, alkylaminocarbonyl, haloalkylsulfonyl, or $C_1$-$C_4$ alkoxy carbonyl; and R is H, $C_1$-$C_6$ alkyl, $C_1$-$C_6$ alkoxy, $C_3$-$C_6$ cycloalkoxy, haloalkyl, alkoxyalkyl, arylalkoxy, alkenyl, alkylthio, alkoxycarbonyl, alkylamino, heteroaryl, arylalkyl, haloalkoxy, aryloxy, or $C_3$-$C_6$ cycloalkyl; and Z is O or S.

The compounds are effective for controlling mites, nematodes, rice planthopper, tobacco budworm, and southern corn rootworm. Methods for making these compounds are also set forth.

U.S. Pat. No. 5,567,723 discloses compounds having the structural formulae

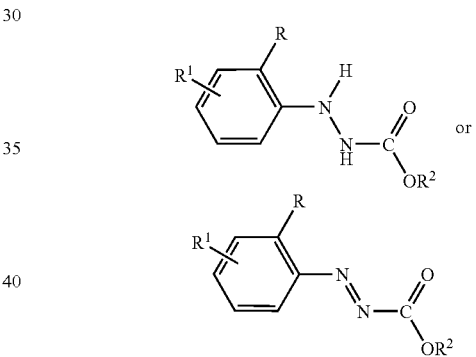

wherein R is $C_1$-$C_6$ alkoxy or $C_1$-$C_6$ alkyl; $R^1$ is fluorenyl, thienyl, pyridyl or thiazolyl, unsubstituted or substituted by one or more substituents selected from $C_1$-$C_4$ alkoxy, $C_1$-$C_4$ alkyl, $C_1$-$C_4$ alkylthio, halogen, $C_1$-$C_4$ haloalkyl and nitro; and $R^2$ is $C_1$-$C_6$ alkyl, $C_3$-$C_6$ cycloalkyl, $C_1$-$C_6$ haloalkyl, $C_2$-$C_6$ alkenyl, or $C_2$-$C_6$ alkoxyalkyl. The compounds are effective for controlling mites and nematodes.

U.S. Pat. No. 6,093,843 discloses compounds having the formula:

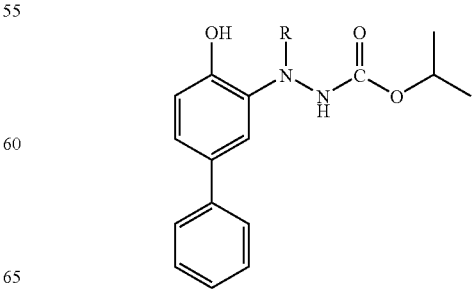

wherein R is hydrogen or $CO_2CH(CH_3)_2$, that are useful as intermediates in the preparation of the miticide bifenazate, methods for their preparation, and methods for the preparation of bifenazate.

U.S. Pat. No. 6,297,275 discloses a method for controlling fungi using a phenylhydrazine derivative compound of the formula:

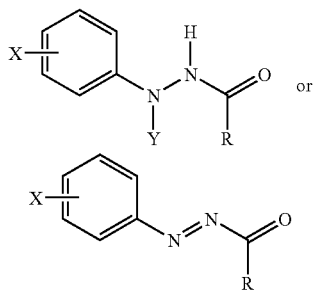

wherein: X is phenyl, phenylalkoxy, phenoxy, or benzyl, alone or in combination with one or more halogen, alkyl, or alkylthio; Y is hydrogen, alkanoyl, haloalkanoyl, or alkoxy carbonyl; and R is hydrogen, alkyl, haloalkyl, alkoxy, haloalkoxy, or phenylalkoxy.

U.S. Pat. No. 6,706,895 discloses a compound having the formula:

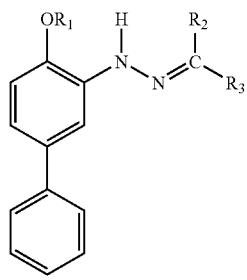

wherein $R_1$ is alkyl and $R_2$ and $R_3$ are independently selected aryl groups. Also disclosed is a method of making bifenazate using the compound as an intermediate.

Canadian Patent No. 1 177 851 discloses arylhydrazoaldoximes which, as such, as tautomers, and in the form of organic or inorganic salts thereof, are said to be active in preventing infections of useful plants by fungi, and in immunizing plants against such infections.

Chinese Patent No. 1035660 discloses an agricultural germicide that is said to be able to inhibit the growth of fungus in Phycomycetes Oomycetes. It is said to be effective for plant diseases resulting from Phycomycetes fungus and the powdery mildew of crops resulting from Ascomycetes. The structural formula is:

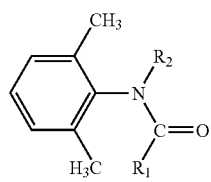

wherein $R_1$ and $R_2$ are as defined in the specification. It is also disclosed that the compound and intermediates can prevent and cure diseases of crops resulting from Phycomycetes fungus and are also effective for downy mildew of cucumber.

U.K. Patent No. 1,160,648 discloses preparations for combating pests that comprise, as active principle, a nitrazone of the formula

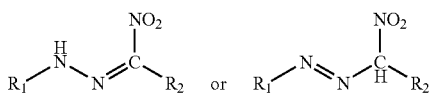

or a salt of such a nitrazone, in which formulae $R_1$ represents a phenyl radical, which may be substituted by a halogen atom or preferably an alkyl group containing 1-4 carbon atoms, $-NO_2$ or preferably an alkoxy radical containing 1-4 carbon atoms or a chlorophenoxy radical or a $CF_3$ radical, and $R_2$ represents an alkyl radical containing 1-4 carbon atoms or a phenyl radical, which may be substituted in the same manner as $R_1$, together with a carrier.

The disclosures of the foregoing are incorporated herein by reference in their entirety.

SUMMARY OF THE INVENTION

The present invention relates to compounds having the formula:

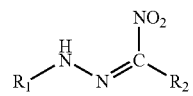

wherein $R_1$ is unsubstituted or substituted biphenyl or a unsubstituted or substituted fluorene or carbazole ring or a unsubstituted or substituted pyridine ring; and $R_2$ is hydrogen or alkyl.

These compounds, or physiologically acceptable salts thereof, are useful as insecticides, acaricides and fungicides.

More particularly, the present invention is directed to a composition of matter comprising a compound of the formula:

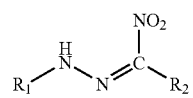

wherein $R_1$ is selected from the group consisting of unsubstituted and substituted biphenyl moieties, unsubstituted and substituted fluorenyl moieties, unsubstituted and substituted carbazolyl moieties, and unsubstituted and substituted pyridyl moieties; and $R_2$ is hydrogen or alkyl.

In another aspect, the present invention is directed to a pesticidal composition comprising:

(A) a pesticidally effective amount of a compound of the formula:

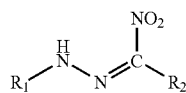

wherein $R_1$ is selected from the group consisting of unsubstituted and substituted biphenyl moieties, unsubstituted and substituted fluorenyl moieties, unsubstituted and substituted carbazolyl moieties, and unsubstituted and substituted pyridyl moieties; and $R_2$ is hydrogen or alkyl; and (B) an acceptable carrier.

In still another aspect, the present invention is directed to a method for controlling undesirable pests comprising applying to a locus to be protected a pesticidally effective amount of a compound of the formula:

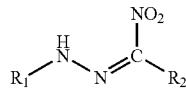

wherein $R_1$ is selected from the group consisting of unsubstituted and substituted biphenyl moieties, unsubstituted and substituted fluorenyl moieties, unsubstituted and substituted carbazolyl moieties, and unsubstituted and substituted pyridyl moieties; and $R_2$ is hydrogen or alkyl.

Preferably, the compounds of the present invention have the formula:

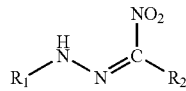

wherein $R_1$ is biphenyl, unsubstituted or monosubstituted by $C_1$-$C_4$ alkyl, $C_1$-$C_6$ alkoxy; or $R_1$ is a fluorene or carbazole ring, unsubstituted or monosubstituted by $C_1$-$C_4$ alkyl; or $R_1$ is a pyridine ring, unsubstituted or monosubstituted by halogen; and $R_2$ is hydrogen or $C_1$-$C_6$ alkyl or branched alkyl.

DESCRIPTION OF THE PREFERRED EMBODIMENTS

As noted above, $R_1$ in the structural formula of the compounds of the present invention can be biphenyl, fluorenyl, carbazolyl, or pyridyl, each of which can be unsubstituted or substituted. If substituted, monosubstitution is preferred.

Where $R_1$ is a substituted biphenyl group, the substituent(s) are preferably selected from the group consisting of alkyl and alkoxy, more preferably $C_1$-$C_4$ alkyl or $C_1$-$C_6$ alkoxy. Such groups may be either straight chain or branched, e.g., methyl, ethyl, propyl, butyl, methoxy, ethoxy, propoxy, butoxy, pentoxy, hexoxy, isomers of the foregoing, and the like.

Where $R_1$ is a substituted fluorenyl or carbazolyl group, the substituent(s) are preferably alkyl, more preferably $C_1$-$C_4$ alkyl. Such groups may be either straight chain or branched, e.g., methyl, ethyl, propyl, butyl, isomers of the foregoing, and the like.

Where $R_1$ is a substituted pyridyl group, the substituent(s) are preferably halogen, e.g., fluorine, chlorine, bromine, or iodine.

Where $R_2$ is alkyl, it can be either branched or straight chain and is preferably alkyl of from 1 to 6 carbon atoms, e.g., methyl, ethyl, propyl, butyl, pentyl, hexyl, isomers of the foregoing, and the like.

The compounds of the present invention can be prepared by the reaction of a suitably substituted amine with sodium nitrite followed by addition of a sodium salt of a nitroalkane:

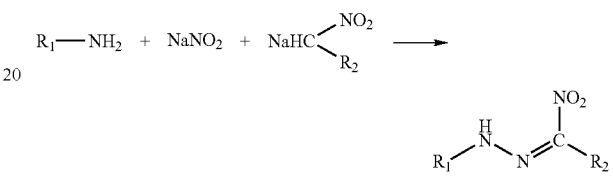

The reaction is conducted in an aqueous medium at temperatures of from about −5 to about 20° C. Following the reaction, the product precipitates, is separated by filtration, and washed with water.

Compositions of the present invention comprise (a) the compound having the structure described above, and (b) a suitable carrier. Such suitable carriers may be solid or liquid in nature.

Suitable liquid carriers may be comprised of water, alcohols, ketones, phenols, toluene, and xylenes. In such formulations, additives conventionally employed in the art can be utilized such as, for example, one or more surface active agents and/or inert diluents, to facilitate handling application of the resulting pesticide composition.

The pesticidal compositions can alternatively comprise solid carriers taking the form of dusts, granules, wettable powders, pastes, aerosols, emulsions, emulsifiable concentrates, and water-soluble solids.

For example, the pesticidal compounds of this invention can be applied as dusts when admixed with or adsorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith can be dispersed in water to form a suspension for application in such form.

Granular formulations of the compounds, suitable for application by broadcasting, side dressing, soil incorporation, or seed treatment, are suitably prepared using a granular or pellitized form of carrier such as granular clays, vermiculite, charcoal, or corn cobs.

Alternatively, the pesticidal compounds can be applied in liquids or sprays when utilized in a liquid carrier, such as in a solution comprising a compatible solvent such as acetone, benzene, toluene, or kerosene, or as dispersed in a suitable non-solvent medium, for example, water.

Another method of application to loci to be treated is aerosol treatment, for which the compound can be dissolved in an aerosol carrier which is a liquid under pressure, but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which can be non-ionic, cationic or anionic. Suitable surface-active agents include those known in the art, such as those disclosed in U.S. Pat. No. 2,547,724 (columns 3 and 4). The compounds of the invention can be mixed with such surface-active dispersing agents, with or without an organic solvent, as concentrates for the subsequent addition of water to yield aqueous suspensions of the compounds at desired concentration levels.

In addition, the compounds can be employed with carriers which themselves are pesticidally active, such as insecticides, acaricides, fungicides, or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound can vary widely. Generally, however, concentrations of the compound as the active ingredient in pesticidally effective formulations can range from about 0.1 to about 95 percent by weight. Spray dilutions can be as low as a few parts per million, while at the opposite extreme, full strength concentrates of the compound can be usefully applied by ultra low volume techniques. Concentration per unit area, where plants constitute the loci of treatment, can range between about 0.01 and about 50 pounds per acre, with concentrations of between about 0.1 and about 10 pounds per acre preferably being employed for crops such as corn, tobacco, rice, and the like.

To combat pests, sprays of the compounds can be applied to the pests directly and/or to plants upon which they feed, grow, or nest. The pesticidally active formulations can also be applied to the soil or other medium in which the pests are present.

Harmful insects, fungi, and acarids attack a wide variety of plants, including both ornamental and agricultural plants and inflict damage by consuming roots and/or foliage, withdrawing vital juices from the plants, secreting toxins, and often by transmitting diseases. The compounds of the present invention can be advantageously utilized to minimize or prevent such damage. The specific methods of application, as well as the selection and concentration of these compounds will, of course, vary depending upon such circumstances as geographic area, climate, topography, plant tolerance, and the like. For specific circumstances, those skilled in the art can readily determine the proper specific compound, concentration, and method of application by routine experimentation.

The compounds of the invention are particularly useful as insecticides, fungicides, and acaricides, for foliar and/or soil application.

The advantages and the important features of the present invention will be more apparent from the following examples.

EXAMPLES

Example 1

Preparation of Propanal, 1-nitro, (4-methoxy-[1,1'-biphenyl]-3-yl)hydrazone

To a suspension of 20.0 grams of 5-phenyl-o-anisidine in 370 mL of water was added 30 mL of concentrated hydrochloric acid and the mixture was stirred for 20 minutes. The mixture was cooled to −5° C. and then a solution of 7.25 grams of sodium nitrite in 50 mL of water was added slowly while maintaining a temperature of −3 to 0° C. The mixture was stirred at 0° C. for 30 minutes and then 82 grams of sodium acetate was added to give 510 mL of a solution of the diazonium acetate. This solution (125 mL) was quickly added to an ice cooled solution of 2.23 grams of 1-nitropropane and 1.0 gram of sodium hydroxide in 40 mL of ethanol and 10 mL of water. This mixture was allowed to warm to room temperature and stirred for 16 hours. The resulting red solid was filtered and washed with water to give 5.7 grams of product whose structure was confirmed by 1 H NMR. The NMR data (ppm) for the compound in DMSO were s(1) 12.5, d(1) 7.8; m(7) 7.5-7.0; s(3) 3.9; q(2) 2.8; t(3) 1.2 and it's structure was:

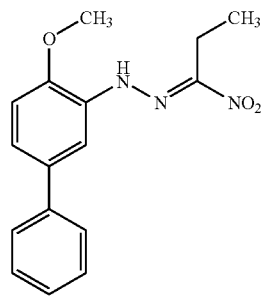

The compounds of Examples 2 through 12 were prepared according to similar procedures.

Example 2

The NMR data (ppm) for the compound in DMSO were s(1) 12.5; d(1) 7.8; m(8) 7.7-6.8; s(3) 3.9 and it's structure was:

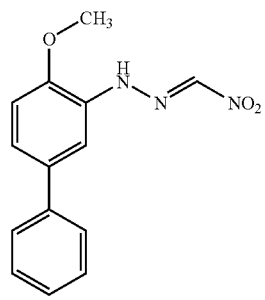

Example 3

The NMR data (ppm) for the compound in DMSO were s(1) 12.5; d(1) 7.8; m(7) 7.7-6.8; s(3) 3.9; t(1) 3.8; t(1) 2.7; m(2) 1.7; m(3) 1.0 and it's structure was:

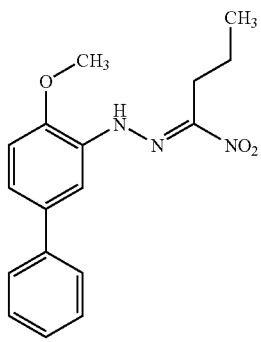

Example 4

The NMR data (ppm) for the compound in DMSO were s(1) 12.2; d(1) 7.8; m(7) 7.6-7.2; s(3) 4.0; m(1) 2.5; d(6) 1.2 and it's structure was:

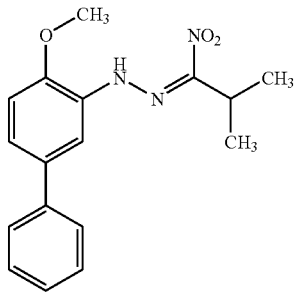

Example 5

The NMR data (ppm) for the compound in DMSO were s(1) 12.3; m(9) 7.5-7.0; q(2) 2.8; t(3) 1.2 and it's structure was:

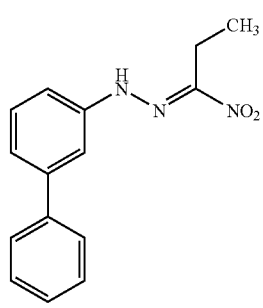

Example 6

The NMR data (ppm) for the compound in DMSO were d(1) 7.8; m(7) 7.5-6.9; t(2) 4.1; q(2) 2.8; m(12) 1.8-0.7 and it's structure was:

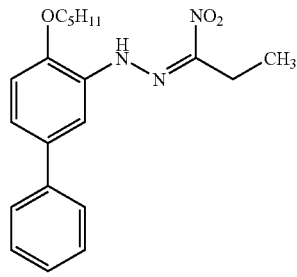

Example 7

The NMR data (ppm) for the compound in DMSO were s(1) 12.4; s(1) 7.9; m(7) 7.6-7.2; q(2) 2.9; s(3) 2.4; t(3) 1.3 and it's structure was:

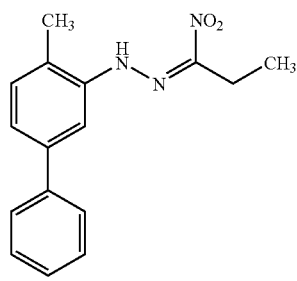

Example 8

The NMR data (ppm) for the compound in DMSO were s(1) 12.6; m(9) 7.6-7.3; d(2) 3.0; m(1) 2.0; d(6) 1.0 and it's structure was:

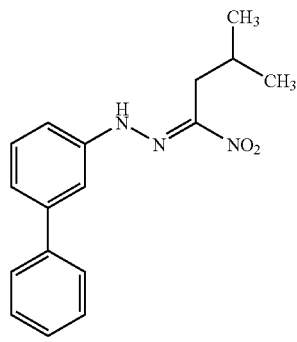

Example 9

The NMR data (ppm) for the compound in DMSO were s(1) 12.4; m(7) 7.5-7.1; d(1) 6.6; s(3) 3.8; q(2) 2.8; t(3) 1.2 and it's structure was:

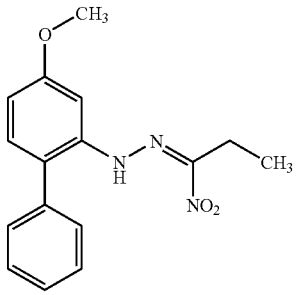

Example 10

The NMR data (ppm) for the compound in DMSO were s(1) 10.4; m(7) 7.7-7.1; s(2) 3.8; s(3) 2.5 and it's structure was:

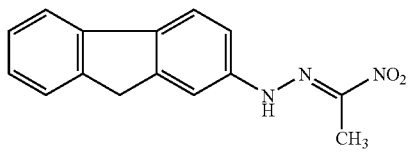

Example 11

The NMR data (ppm) for the compound in DMSO were s(1) 12.7; m(2) 8.0; m(5) 7.3; q(2) 4.2; q(2) 2.8; t(6) 1.3 and it's structure was:

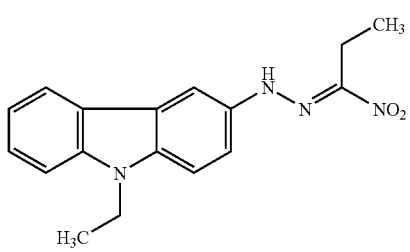

Example 12

The NMR data (ppm) for the compound in DMSO were s(1) 12.7; d(1) 8.3; m(2) 7.5; q(2) 2.9; t(3) 1.1 and it's structure was:

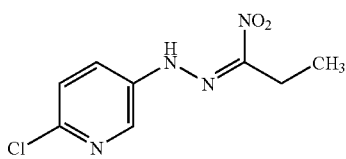

Biological Data for Insecticides

Stock Solution Preparation

In the following examples, a stock solution for the compounds of the present invention was prepared at 3000 ppm by dissolving 0.24 gram of each compound to be tested in eight mL of acetone and adding 72 mL of distilled water plus three drops of ethoxylated sorbitan monolaurate, a wetting agent. This stock solution was used to demonstrate the pesticidal use of representative compounds of this invention. For each example that follows, the stock solution was used and the specificized dilutions made. All the tests discussed below, which involved treatment with compounds of this invention, were always repeated with controls, in which the active compound was not provided, to permit a comparison upon which the percent control was calculated.

Example 13

Mite Adulticide and Mite Ovicide Tests

One day before treatment of cowpea primary leaves with the test solutions, a "Figure 8" configuration of tree tanglefoot was applied to each of two cowpea primary leaves, one from each of two plants in a pot. The circle nearer the stem was designated for the mite ovicide test and the circle further from the stem was designated for the mite adulticide test.

Groups of adult mites (*Tetranychus urticae* Koch) were transferred into ovicide circles one day before treatment and the females were allowed to deposit eggs until one hour before treatment, at which point all the adults were removed. The plants were then sprayed to run off with a 1000 ppm of solution diluted from the 3000 ppm stock solution.

One day following treatment of the plants with the test solution, groups of approximately 25 adult mites were transferred into the adulticide rings. Five days later, these rings were examined for live mites remaining on the leaves. The percent control was estimated based on the number of mites surviving on the control plants.

Nine days following treatment the ovicide rings were examined for unhatched eggs and living immature mites. The percent control was estimated based on the number of unhatched eggs.

Results of the mite adulticide (MI) and ovicide (MIOV) tests are presented below in Table 1.

Example 14

Tobacco Budworm Test

For each compound tested, 0.2 mL of the stock solution prepared asdescribed above, was pipetted onto the surface of each of five diet cells, allowed to spread over the surfaces and air dried for two hours. Then a second instar *Helicoverpa virescens* larva was introduced into each cell. After 14 days, the number of living larvae was determined for each treatment and percent control, corrected by Abbott's formula, was calculated.

The results of the testing of tobacco budworms (TB) are presented in Table 1 below.

TABLE 1

| Compound Number | Pesticidal Activity Percent Control | | |
|---|---|---|---|
| | MI | MIOV | TB |
| 1 | 100 | 100 | 64 |
| 2 | 0 | 0 | 100 |
| 3 | 100 | 100 | 0 |
| 4 | 100 | 0 | 0 |
| 5 | 100 | 0 | 0 |
| 6 | 100 | 30 | 0 |
| 7 | 100 | 70 | 0 |
| 8 | 100 | 0 | 40 |
| 9 | 70 | 70 | 14 |
| 10 | 0 | 0 | 0 |
| 11 | 30 | 30 | 57 |
| 12 | 100 | 70 | 100 |

In view of the many changes and modifications that can be made without departing from principles underlying the invention, reference should be made to the appended claims for an understanding of the scope of the protection to be afforded the invention.

What is claimed is:

1. A composition comprising a compound of the formula:

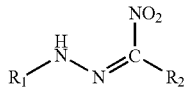

wherein
  $R_1$ is unsubstituted or substituted biphenyl; and
  $R_2$ is hydrogen or alkyl.

2. The composition of claim 1 wherein $R_1$ is biphenyl, unsubstituted or monosubstituted by $C_1$-$C_4$ alkyl, $C_1$-$C_6$ alkoxy and $R_2$ is hydrogen or $C_1$-$C_6$ alkyl or branched alkyl.

3. The composition of claim 2 wherein $R_1$ is unsubstituted biphenyl.

4. The composition of claim 2 wherein $R_1$ is monosubstituted biphenyl.

5. The composition of claim 1 wherein the compound is of the structure:

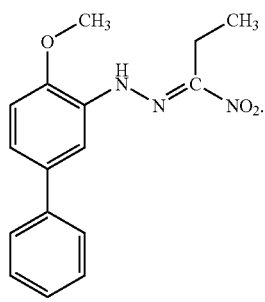

6. A pesticidal composition comprising:
(A) a pesticidally effective amount of a compound of the formula:

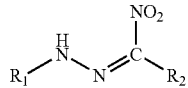

wherein:
  $R_1$ is unsubstituted or substituted biphenyl; and
  $R_2$ is hydrogen or alkyl; and
(B) an acceptable carrier.

7. The composition of claim 6 wherein:
  $R_1$ is biphenyl, unsubstituted or monosubstituted by $C_1$-$C_4$ alkyl, $C_1$-$C_6$ alkoxy; and
  $R_2$ is hydrogen or $C_1$-$C_6$ alkyl or branched alkyl.

8. The composition of claim 7 wherein $R_1$ is unsubstituted biphenyl.

9. The composition of claim 7 wherein $R_1$ is monosubstituted biphenyl.

10. The composition of claim 6 wherein the compound is of the structure:

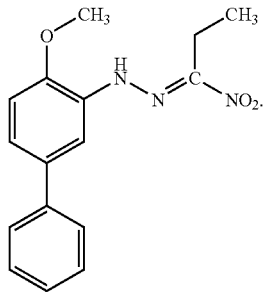

11. A method for controlling undesirable pests comprising applying to a locus to be protected a pesticidally effective amount of a compound of the formula:

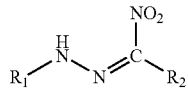

wherein
  $R_1$ is unsubstituted or substituted biphenyl; and
  $R_2$ is hydrogen or alkyl.

12. The method of claim 11 wherein
  $R_1$ is biphenyl, unsubstituted or monosubstituted by $C_1$-$C_4$ alkyl, $C_1$-$C_6$ alkoxy; and
  $R_2$ is hydrogen or $C_1$-$C_6$ alkyl or branched alkyl.

13. The method of claim 12 wherein $R_1$ is unsubstituted biphenyl.

14. The method of claim 12 wherein $R_1$ is monosubstituted biphenyl.

15. The method of claim 11 wherein the compound is of the structure:

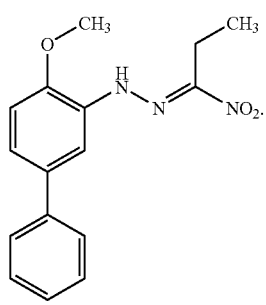
16. The composition of claim 6, wherein the carrier is selected from the group consisting of liquid carriers and solid carriers.
17. The composition of claim 6, wherein the pesticidally effective amount is from about 0.1 to about 95 percent by weight.
* * * * *